United States Patent
Mallory et al.

(10) Patent No.: US 10,709,322 B2
(45) Date of Patent: Jul. 14, 2020

(54) LARYNGOSCOPE WITH INTEGRATED AND CONTROLLABLE SUCTION

(71) Applicants: University of Louisville Research Foundation, Inc., Louisville, KY (US); InScope Medical Solutions, Inc., New Albany, NY (US)

(72) Inventors: Mary Nan Mallory, Louisville, KY (US); Benjamin Cunningham, Louisville, KY (US); Adam Casson, Brooklyn, NY (US)

(73) Assignees: UNIVERSITY OF LOUISVILLE RESEARCH FOUNDATION, INC., Louisville, KY (US); INSCOPE MEDICAL SOLUTIONS, INC., New Albany, IN (US)

( * ) Notice: Subject to any disclaimer, the term of this patent is extended or adjusted under 35 U.S.C. 154(b) by 181 days.

(21) Appl. No.: 15/114,986

(22) PCT Filed: Jan. 30, 2015

(86) PCT No.: PCT/US2015/013690
§ 371 (c)(1),
(2) Date: Jul. 28, 2016

(87) PCT Pub. No.: WO2015/116900
PCT Pub. Date: Aug. 6, 2015

(65) Prior Publication Data
US 2016/0345803 A1     Dec. 1, 2016

Related U.S. Application Data

(60) Provisional application No. 61/934,113, filed on Jan. 31, 2014.

(51) Int. Cl.
*A61B 1/267*     (2006.01)
*A61B 1/00*     (2006.01)
(Continued)

(52) U.S. Cl.
CPC .......... *A61B 1/267* (2013.01); *A61B 1/00016* (2013.01); *A61B 1/00068* (2013.01);
(Continued)

(58) Field of Classification Search
CPC ...................................................... A61B 1/267
(Continued)

(56) References Cited

U.S. PATENT DOCUMENTS 3,848,587 A * 11/1974 McDonald ............. A61B 1/227
600/187
5,702,351 A   12/1997 Bar-Or et al.
(Continued)

FOREIGN PATENT DOCUMENTS

AU   2015210829 A1   8/2016
CA     2937890 A1    8/2015
(Continued)

OTHER PUBLICATIONS

PCT/US2015/013690 International Search Report and Written Opinion dated May 6, 2015, 8 pages.
(Continued)

*Primary Examiner* — Amy R Sipp
(74) *Attorney, Agent, or Firm* — Nixon Peabody LLP

(57) ABSTRACT

A laryngoscope with integrated and controllable suction includes a handle and a blade. A suction port is at the proximal end of the handle and is configured for connection to an air source. The suction port defines an opening into one or more air flow paths defined through the laryngoscope, which each terminate at one or more intake ports. In some embodiments, a valve is interposed into each air flow path to regulate air flow along each air flow path. Such a valve is operably connected to a switch mounted on an exterior surface of the laryngoscope, such that manipulation of the switch causes the valve to open or close, thus allowing the
(Continued)

physician or other medical professional to control the air flow and selectively apply constant or intermittent suction.

9 Claims, 11 Drawing Sheets

(51) Int. Cl.
*A61B 1/015* (2006.01)
*A61B 1/05* (2006.01)
*A61B 1/12* (2006.01)
*A61B 1/06* (2006.01)

(52) U.S. Cl.
CPC .......... *A61B 1/00094* (2013.01); *A61B 1/015* (2013.01); *A61B 1/05* (2013.01); *A61B 1/0676* (2013.01); *A61B 1/126* (2013.01)

(58) Field of Classification Search
USPC ..................................... 600/185–200, 205
See application file for complete search history.

(56) References Cited

U.S. PATENT DOCUMENTS

| | | | | |
|---|---|---|---|---|
| 5,897,489 | A | * | 4/1999 | Urbanowicz ........ A61B 1/0014 600/185 |
| 6,106,458 | A | * | 8/2000 | Ha ........................ A61B 1/267 600/185 |
| 7,608,040 | B1 | * | 10/2009 | Dunst .................... A61B 1/267 600/104 |
| 2001/0051766 | A1 | | 12/2001 | Gazdzinski |
| 2002/0022769 | A1 | | 2/2002 | Smith et al. |
| 2002/0082475 | A1 | | 6/2002 | Stahl et al. |
| 2007/0287888 | A1 | | 12/2007 | Lovell et al. |
| 2010/0121152 | A1 | | 5/2010 | Boedeker |
| 2010/0256482 | A1 | | 10/2010 | Peters et al. |
| 2010/0261968 | A1 | | 10/2010 | Nearman et al. |
| 2011/0028790 | A1 | * | 2/2011 | Farr ................... A61B 1/00052 348/77 |
| 2011/0092773 | A1 | * | 4/2011 | Goldstein ............. A61B 1/015 600/187 |
| 2011/0130627 | A1 | | 6/2011 | McGrail et al. |
| 2011/0178372 | A1 | | 7/2011 | Pacey et al. |
| 2012/0035502 | A1 | | 2/2012 | Menegazzi |
| 2013/0060090 | A1 | | 3/2013 | McGrath et al. |
| 2013/0104884 | A1 | | 5/2013 | Vazales et al. |
| 2013/0197312 | A1 | * | 8/2013 | Miller .................... A61B 1/267 600/188 |
| 2016/0000300 | A1 | | 1/2016 | Williams |
| 2018/0214013 | A1 | | 8/2018 | Casson |

FOREIGN PATENT DOCUMENTS

| | | |
|---|---|---|
| CA | 3015226 A1 | 9/2017 |
| CN | 1452472 A | 10/2003 |
| CN | 102481086 A | 5/2012 |
| CN | 106132281 A | 11/2016 |
| CN | 108697318 A | 10/2018 |
| EP | 3099216 A1 | 12/2016 |
| EP | 3331420 | 6/2018 |
| EP | 3422925 A | 1/2019 |
| JP | 2017504465 A | 2/2017 |
| MX | 2016009802 A | 1/2017 |
| TH | 177022 | 6/2018 |
| WO | 2012172076 A1 | 12/2012 |
| WO | 2014105649 A1 | 7/2014 |
| WO | 2015116900 A1 | 8/2015 |
| WO | 2017024007 A1 | 2/2017 |
| WO | 2017151796 A1 | 9/2017 |

OTHER PUBLICATIONS

PCT/US2015/013690 International Preliminary Report on Patentability dated Aug. 2, 2016, 7 pages.
EP Extended Search Report for 15743864.9 dated Aug. 30, 2017, 6 pages.
International Search Report and Written Opinion for PCT/US2016/045299 dated Oct. 26, 2016, 13 pages.
International Search Report and Written Opinion for PCT/US2017/020242 dated May 15, 2017, 22 pages.
International Preliminary Report on Patentability for PCT/US2016/045299 dated Feb. 6, 2018, 11 pages.
International Preliminary Report on Patentability for PCT/US2017/020242 dated Sep. 4, 2018.
EP Examination Report for EP 15743864.9 dated Jan. 22, 2019, 3 pages.

* cited by examiner

LARYNGOSCOPE WITH INTEGRATED AND CONTROLLABLE SUCTION

CROSS-REFERENCE TO RELATED APPLICATIONS

This application is a National Phase of International Application No. PCT/US2015/013690, filed Jan. 30, 2015, which designated the U.S. and that International Application was published under PCT Article 21(2) in English, which claims priority under 35 U.S.C. § 119(e) to U.S. Provisional Application No. 61/934,113, filed Jan. 31, 2014, the contents of which are hereby incorporated herein by reference in their entirety.

BACKGROUND OF THE INVENTION

The present invention relates to devices for performing a laryngoscopy.

A laryngoscopy is a medical procedure used to view and examine the interior of the larynx (or voice box), including the glottis and vocal cords. A laryngoscopy is often used to identify tumors, structural damage to the glottis or vocal cords, or other abnormalities.

In a direct laryngoscopy, a laryngoscope is inserted into the mouth of a patient and then manipulated to allow a physician or other medical professional a direct line of sight to view the glottis and vocal cords.

In an indirect laryngoscopy, the laryngoscope carries a fiber-optic or digital camera of some form, so that a physician can view an image of the glottis and vocal cords. In many cases, due to the health condition of the patient, indirect laryngoscopies are often the best option and/or are medically necessary. For instance, indirect laryngoscopies are particularly helpful in the growing geriatric population, many with inflexible cervical spines. Indirect laryngoscopies are also useful for pregnant women, trauma victims, and obese patients.

With respect to the construction of a laryngoscope, a laryngoscope is commonly comprised of a handle and a blade. The handle is the portion of the laryngoscope that extends out of the mouth and is manipulated by a physician or other medical professional. The blade is inserted into the airway and is used to lift the epiglottis and/or position the lens of the camera to view the glottis and vocal cords.

In certain medical situations, it may be necessary to perform a tracheal intubation (or intubation) on a patient in which an endotracheal tube is inserted into the trachea to maintain an open airway. A laryngoscopy is commonly performed to assist in such intubation. For instance, in emergency situations, such as care performed in an ambulance or medical helicopter, the airway of a patient may be partially filled with blood or other secretions. Indeed, since the throat is not visualized until the laryngoscope is placed, fluids such as blood, vomit, mucus, and saliva may be pooled and blocking the view of the target vocal cords. Even when the view is initially clear, secretions may accumulate at any time, often quite unexpectedly. Thus, the physician or other medical professional (e.g., paramedic or flight nurse) may need to provide suction before being able to successfully visualize the target vocal cords for intubation. Manipulation of the endotracheal tube requires the use of the right hand of the physician or other medical professional during the intubation, while the left hand is operating the laryngoscope. In order to provide suction, the right hand must switch between manipulating the endotracheal tube and a separate suction catheter, often causing delays in completing the intubation. Furthermore, the lens of the camera at the distal end of the fiber-optic or video-aided laryngoscope may become covered with blood or other secretions, rendering the technology ineffective. Thus, there remains a need for a laryngoscope that addresses some of the deficiencies of prior art technologies.

SUMMARY OF THE INVENTION

The present invention is a laryngoscope with integrated and controllable suction.

An exemplary laryngoscope with integrated and controllable suction made in accordance with the present invention generally includes a handle and a blade. Again, the handle is the portion of the laryngoscope that extends out of the mouth and is manipulated by a physician or other medical professional. The blade is inserted into the airway and is used to lift the epiglottis and/or position the lens of the camera to view the glottis and vocal cords.

The exemplary laryngoscope further includes a suction port at the proximal end of the handle, i.e., at a position that would be outside of the mouth of a patient during use. This suction port is configured for connection to an air source, for example, via a length of tubing. Furthermore, the suction port defines an opening into one or more air flow paths defined through the laryngoscope, which each terminate at one or more intake ports.

In some embodiments, a valve is interposed into each air flow path to regulate air flow along the air flow path. Such a valve is operably connected to a switch mounted on an exterior surface of the laryngoscope, such that manipulation of the switch causes the valve to open or close, thus allowing the physician or other medical professional to control the air flow and selectively apply constant or intermittent suction.

In some embodiments, a first air flow path extends down the handle of the laryngoscope, along the length of the blade, and then terminates at one or more intake ports positioned at a distal end (or tip) of the blade of the laryngoscope.

In some embodiments, a second air flow path extends down the handle of the laryngoscope, along the length of the blade, and then terminates at one or more intake ports positioned on the bottom surface of the blade near a camera lens.

With respect to the camera lens, in some embodiments, a camera is housed within the blade, with the camera lens oriented to look toward the distal end of the blade. The camera is intended to provide a view of the glottis and vocal cords as the blade of the laryngoscope is inserted into the airway and used to lift the epiglottis, and thus, an exemplary laryngoscope may include a wireless transceiver for transmitting images acquired during use of the laryngoscope to a remote display. And, because of the positioning of the intake ports, constant or intermittent suction can be applied to remove secretions in the vicinity of the camera lens and maintain a clear view.

As a further refinement, to assist the physician or other medical professional in the use of the laryngoscope, in some embodiments, the laryngoscope may also be provided with a light, such as a light-emitting diode (LED), that is positioned and directed to emit light down and along the blade of the laryngoscope.

In practice, the laryngoscope may be maintained in sealed packaging (i.e., a sterile environment) until use. When needed, the laryngoscope is removed from its packaging, a length of tubing is used to connect the suction port of the laryngoscope to an air source, and the laryngoscope is then introduced in the mouth of the patient.

While holding the laryngoscope in one hand (e.g., the left hand), the physician or other medical professional can use his/her finger to manipulate the switch to provide either intermittent or continuous suction, for example, via (i) a first air flow path and intake ports to provide suction at the distal end (or tip) of the blade, and/or (ii) a second air flow path and intake ports to provide suction in the vicinity of a camera lens.

As a result of integrating suction functionality into the laryngoscope of the present invention, the physician or other medical professional can use one hand to operate the laryngoscope and provide suction, while the right hand is used to manipulate an endotracheal tube or for another purpose, such as externally manipulating the larynx to assist in image acquisition, retrieving foreign bodies from the airway, or performing a biopsy. Furthermore, the suction functionality is already in the mouth and immediately ready when needed, optimizing the speed at which suctioning of fluids that may be otherwise aspirated into the lungs.

DETAILED DESCRIPTION OF THE INVENTION

The present invention is a laryngoscope with integrated and controllable suction.

Figure 1:
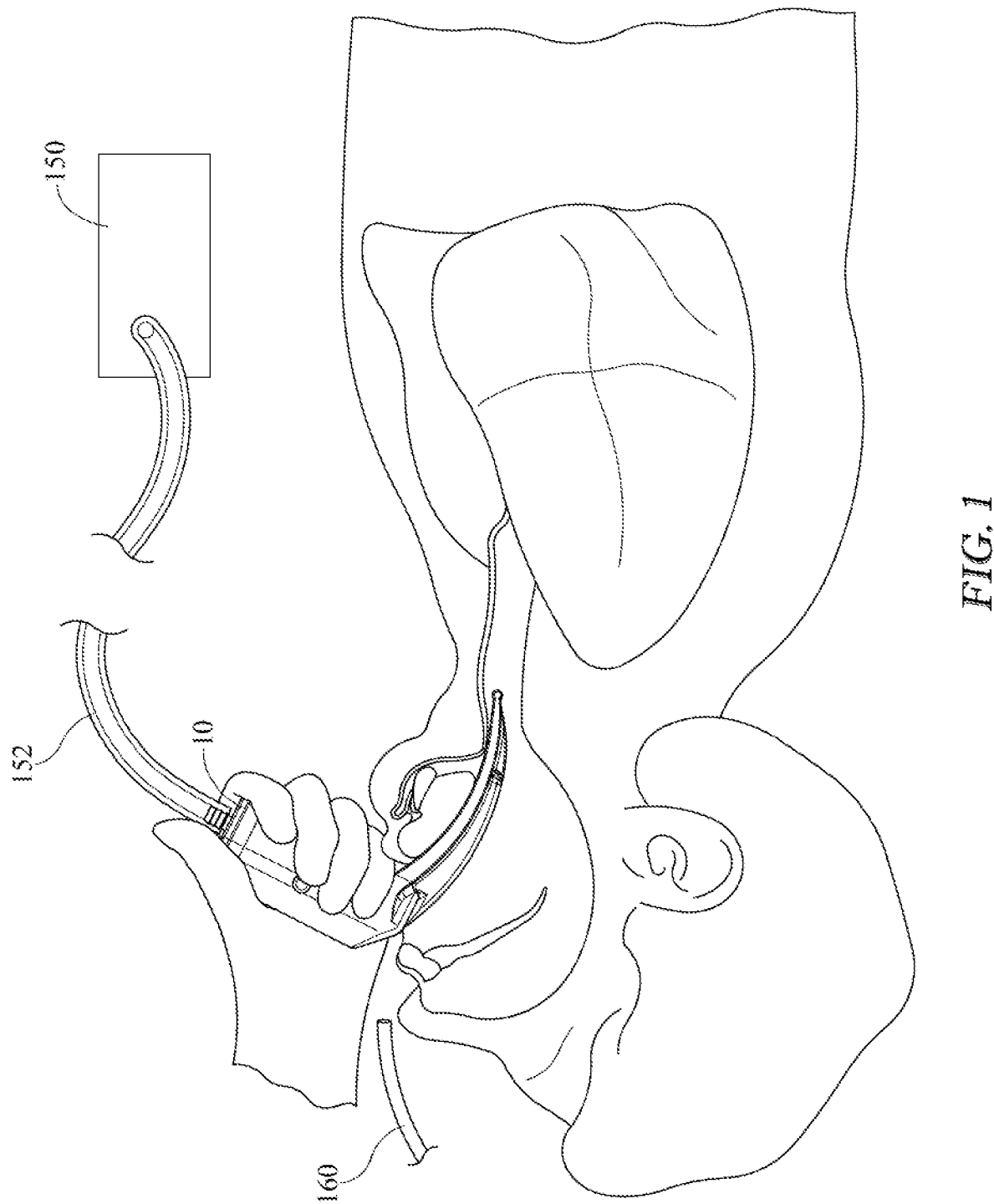
FIG. 1 is a view of an exemplary laryngoscope made in accordance with the present invention, as inserted into the mouth and throat of a patient.
Figure 2:
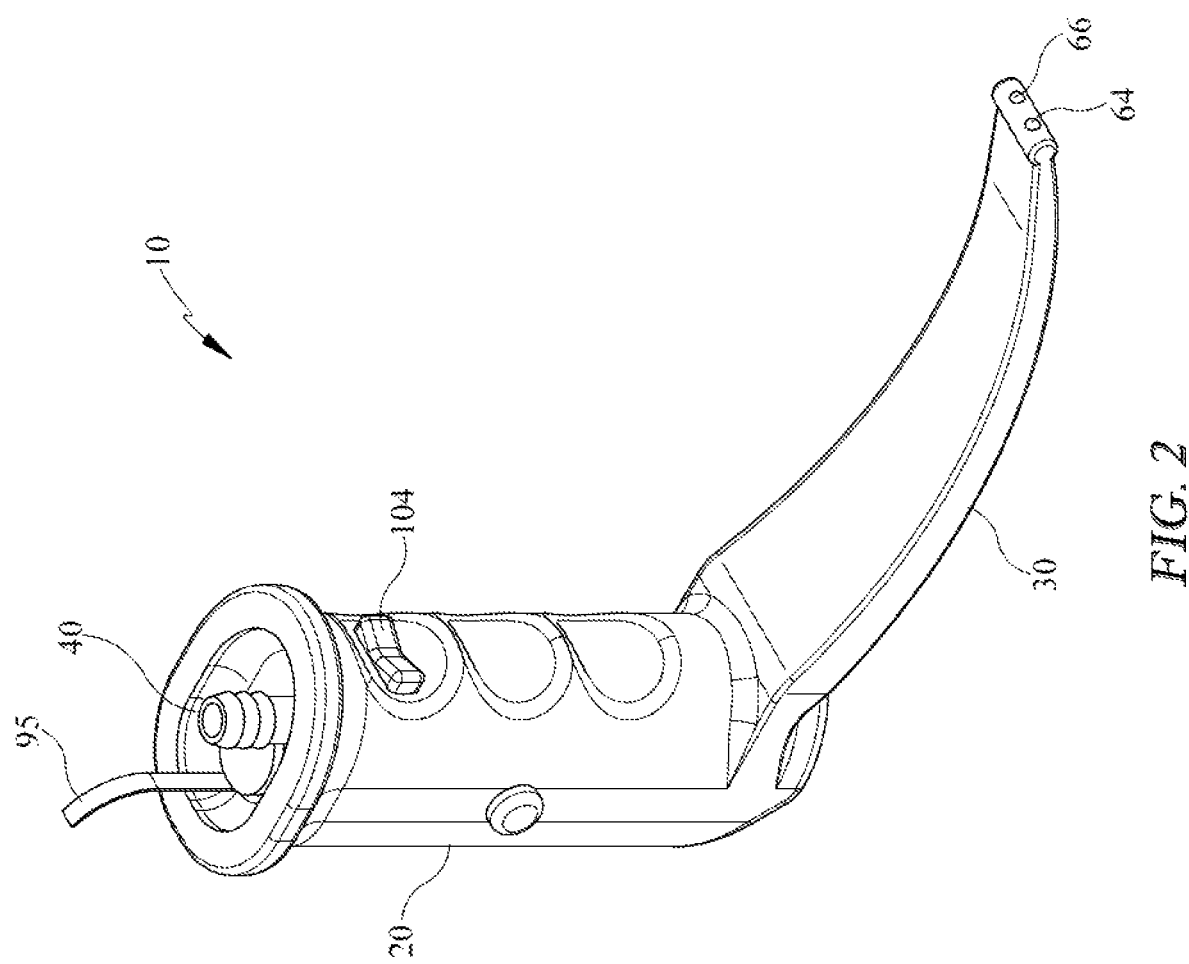
FIG. 2 is a perspective view of an exemplary laryngoscope made in accordance with the present invention.

FIGS. 1-7 and 7A-7B are various views of an exemplary laryngoscope 10 with integrated and controllable suction made in accordance with the present invention. As shown, the exemplary laryngoscope 10 generally includes a handle 20 and a blade 30. The handle 20 is the portion of the laryngoscope 10 that extends out of the mouth and is manipulated by a physician or other medical professional, as best shown in FIG. 1. The blade 30 is inserted into the airway and is used to lift the epiglottis and/or position the lens of a camera (as further described below) to view the glottis and vocal cords, as also shown in FIG. 1. In this exemplary embodiment, the handle 20 and the blade 30 are an integral component molded from a thermoplastic; however, the handle 20 and the blade 30 could be made of other materials and/or constructed as separate and discrete components that are fastened together without departing from the spirit and scope of the present invention.

Referring now to FIGS. 2-7, the laryngoscope 10 includes a suction port 40 at the proximal end of the handle 20, i.e., at a position that would be outside of the mouth of a patient during use. This suction port 40 is configured for connection to an air source 150 (FIG. 1), for example, via a length of tubing 152 (FIG. 1). In this regard, an air source providing suction is commonly and readily available in hospital emergency rooms, ambulances, medical helicopters, and other care facilities. The suction port 40 defines an opening into an upper internal channel 42 defined by the handle 20 of the laryngoscope 10. The upper internal channel 42 is in fluid communication with first and second valves 50, 52, each of which control access to subsequent internal channels which define flow paths through the handle 20, through the blade 30, and to respective intake ports, as further described below.

Figure 7:
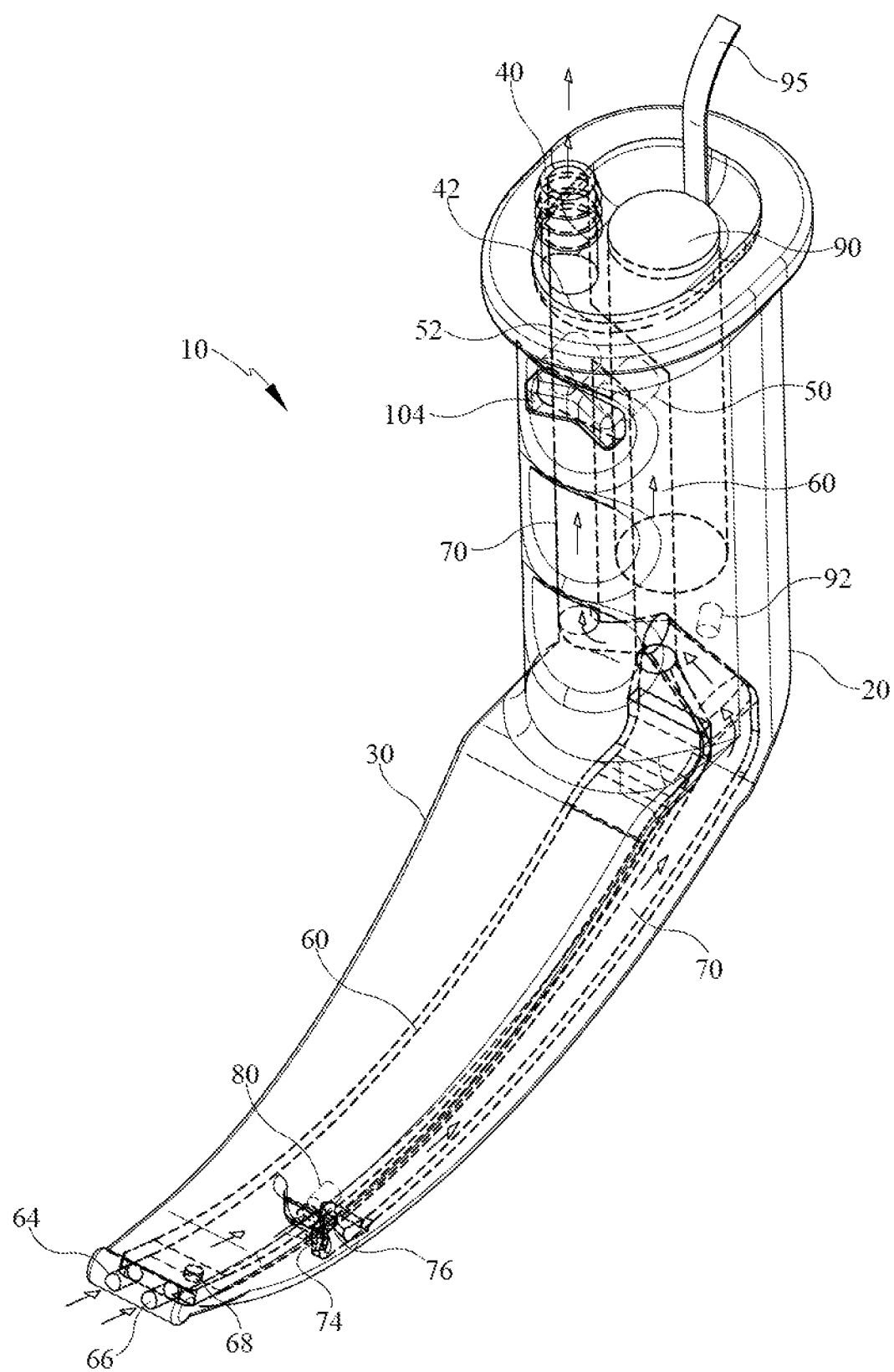
FIG. 7 is an alternate perspective view of the exemplary laryngoscope of FIG. 1 that further illustrates the first and second air flow paths and certain internal components of the exemplary laryngoscope.
Figure 7A:
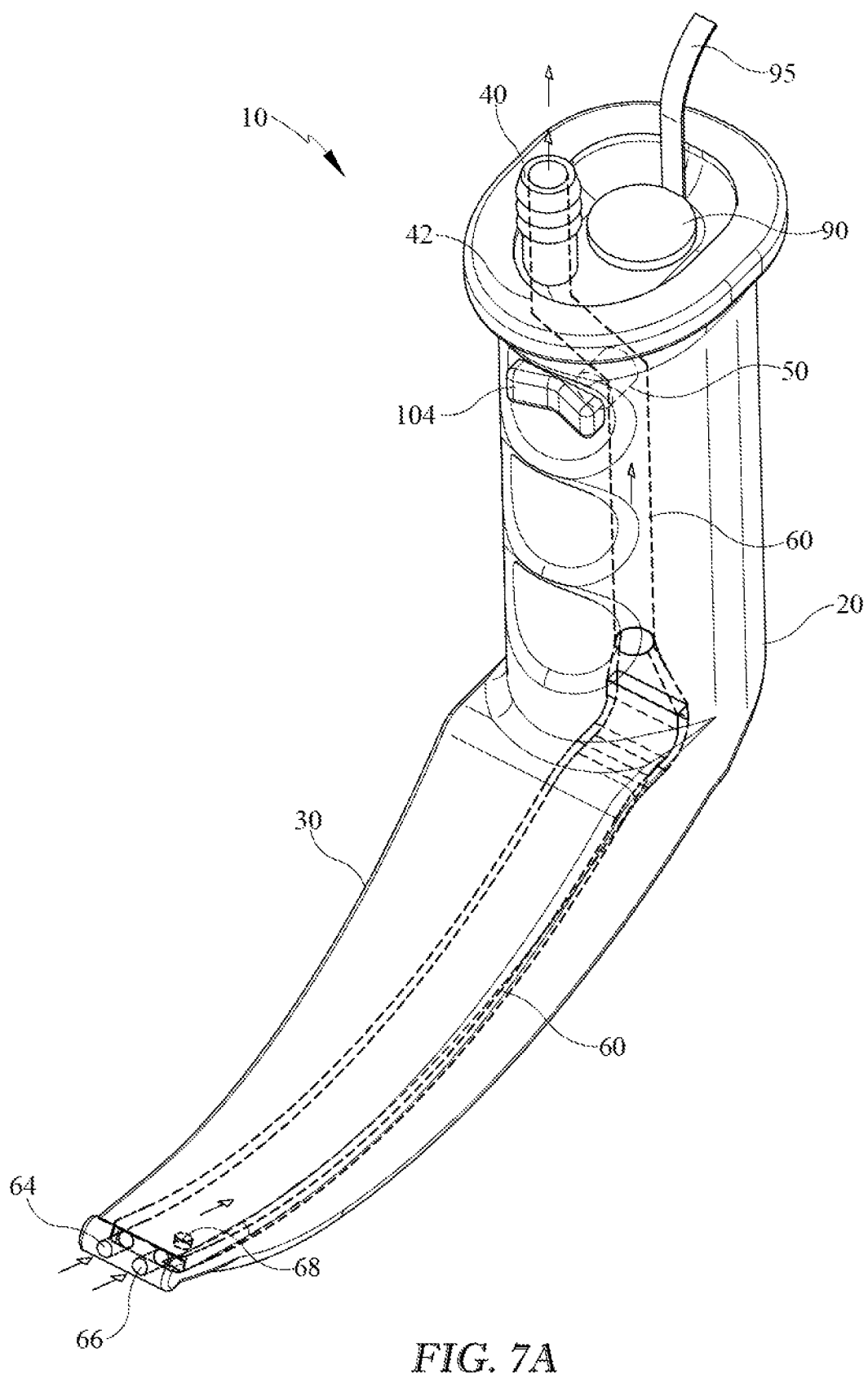
FIG. 7A is similar to FIG. 7, but illustrates the first air flow path alone.

Specifically, in this exemplary embodiment, and as best shown in FIGS. 7 and 7A, when the first valve 50 is open, the upper internal channel 42 is placed in fluid communication with a first (lower) internal channel 60 that defines a first air flow path that extends down the handle 20 of the laryngoscope 10 and then along the length of the blade 30. This first air flow path terminates at three intake ports 64, 66, 68 positioned at a distal end (or tip) of the blade 30 of the laryngoscope 10. In this case, two intake ports 64, 66 are along the leading edge of the tip of the blade 30, while the third intake port 68 is along the bottom surface of the blade 30. Thus, the intake ports 64, 66, 68 are well-positioned to provide constant or intermittent suction and remove blood or other secretions during a laryngoscopy and intubation, as further described below.

Figure 7B:
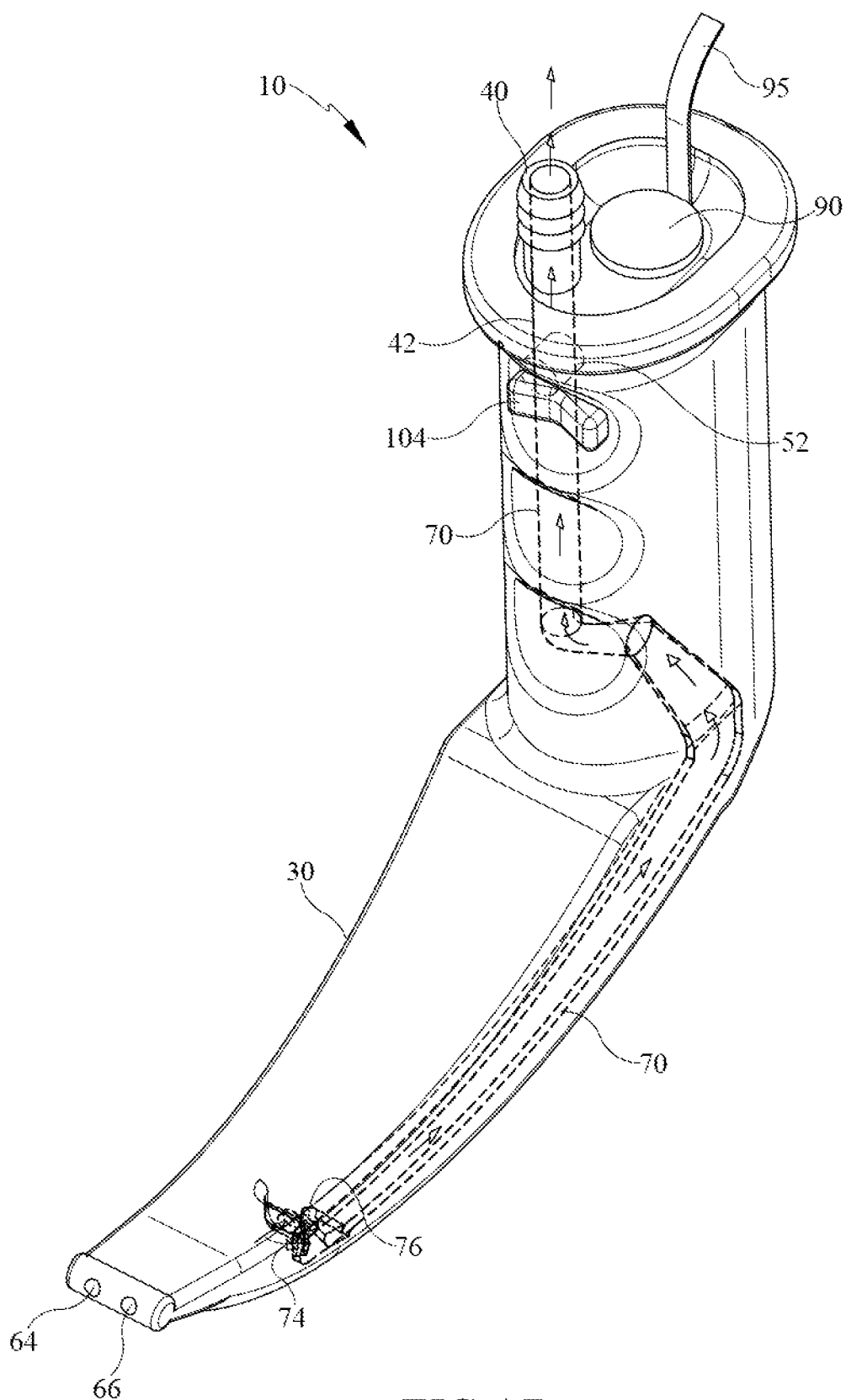
FIG. 7B is similar to FIG. 7, but illustrates the second air flow path alone.

In this exemplary embodiment, and as best shown in FIGS. 7 and 7B, when the second valve 52 is open, the upper internal channel 42 is placed in fluid communication with a second (lower) internal channel 70 that defines a second air flow path that extends down the handle 20 of the laryngoscope 10 and then along the length of the blade 30, in this case, along a lateral edge of the blade 30. This second air flow path terminates at two intake ports 74, 76, positioned on the bottom surface of the blade near a camera lens 82.

Figure 3:
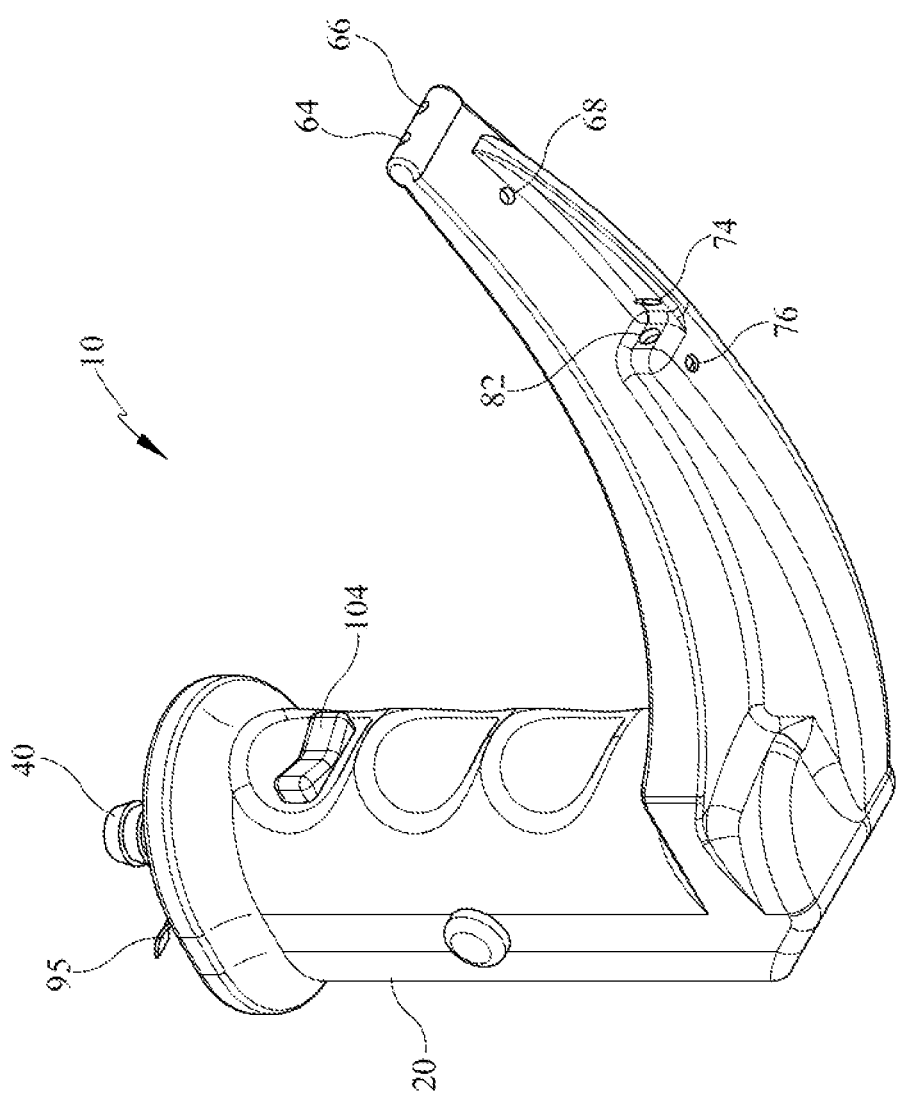
FIG. 3 is an alternate (bottom) perspective view of the exemplary laryngoscope of FIG. 1.
Figure 4:
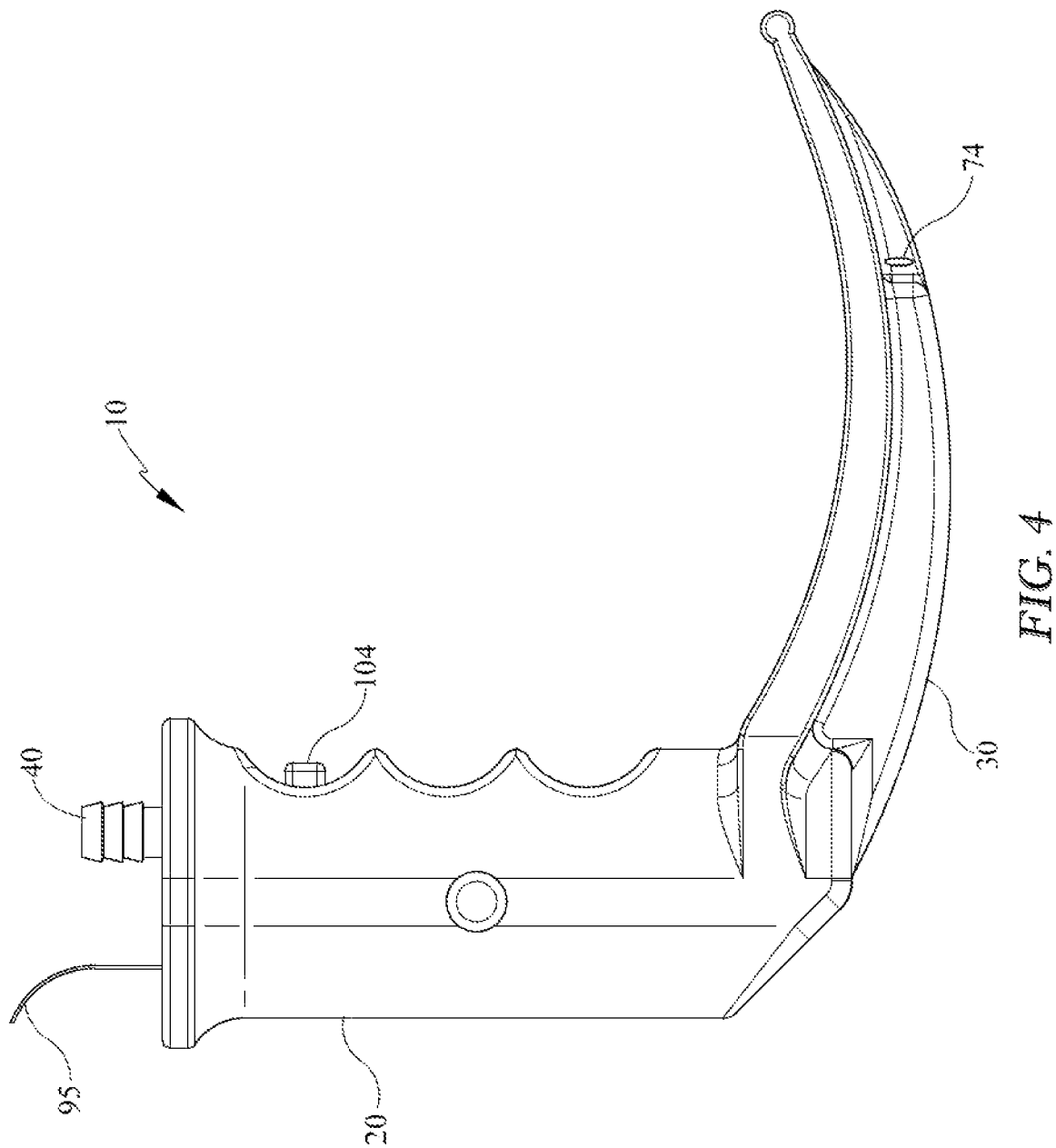
FIG. 4 is a side view of the exemplary laryngoscope of FIG. 1.
Figure 5:
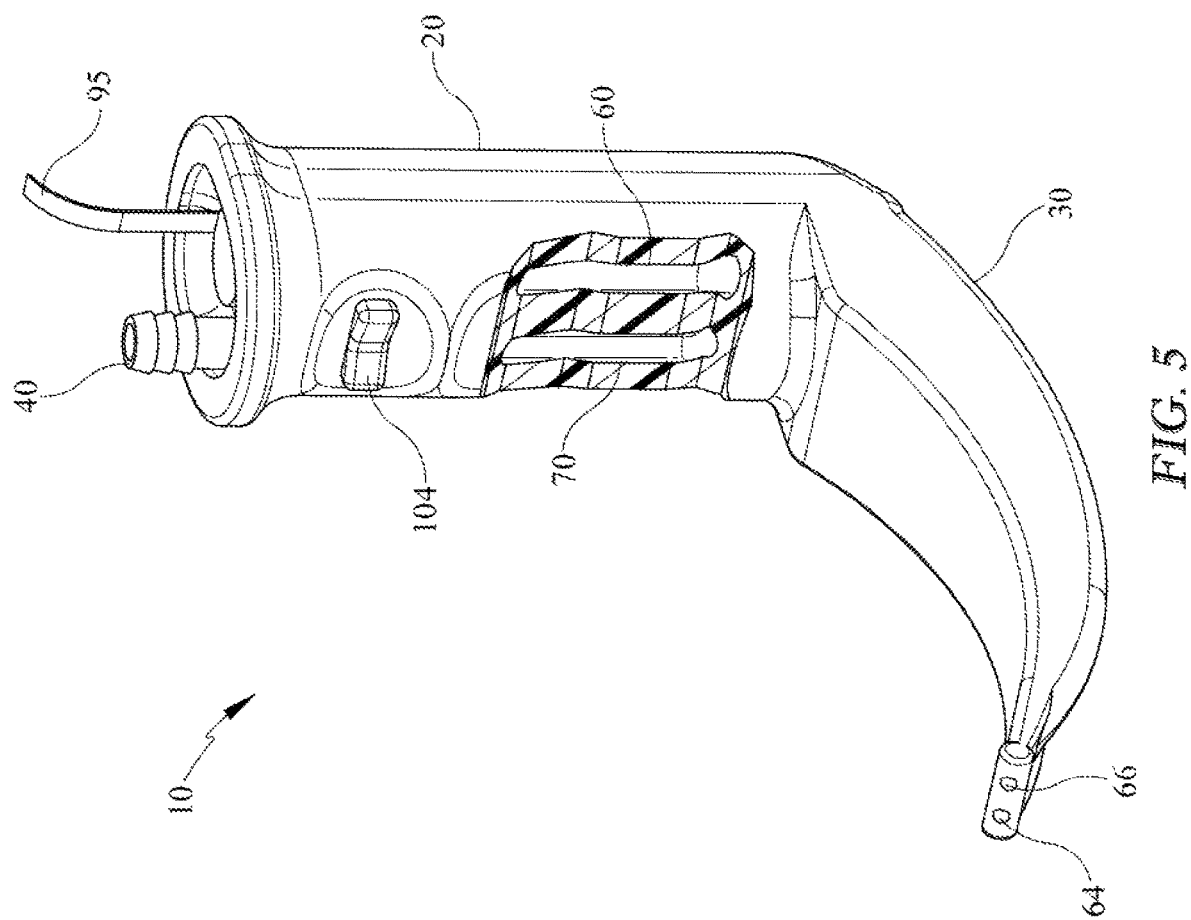
FIG. 5 is an alternate perspective view of the exemplary laryngoscope of FIG. 1, with a portion of the handle cutaway to illustrate the first and second internal channels that define the first and second air flow paths.
Figure 6:
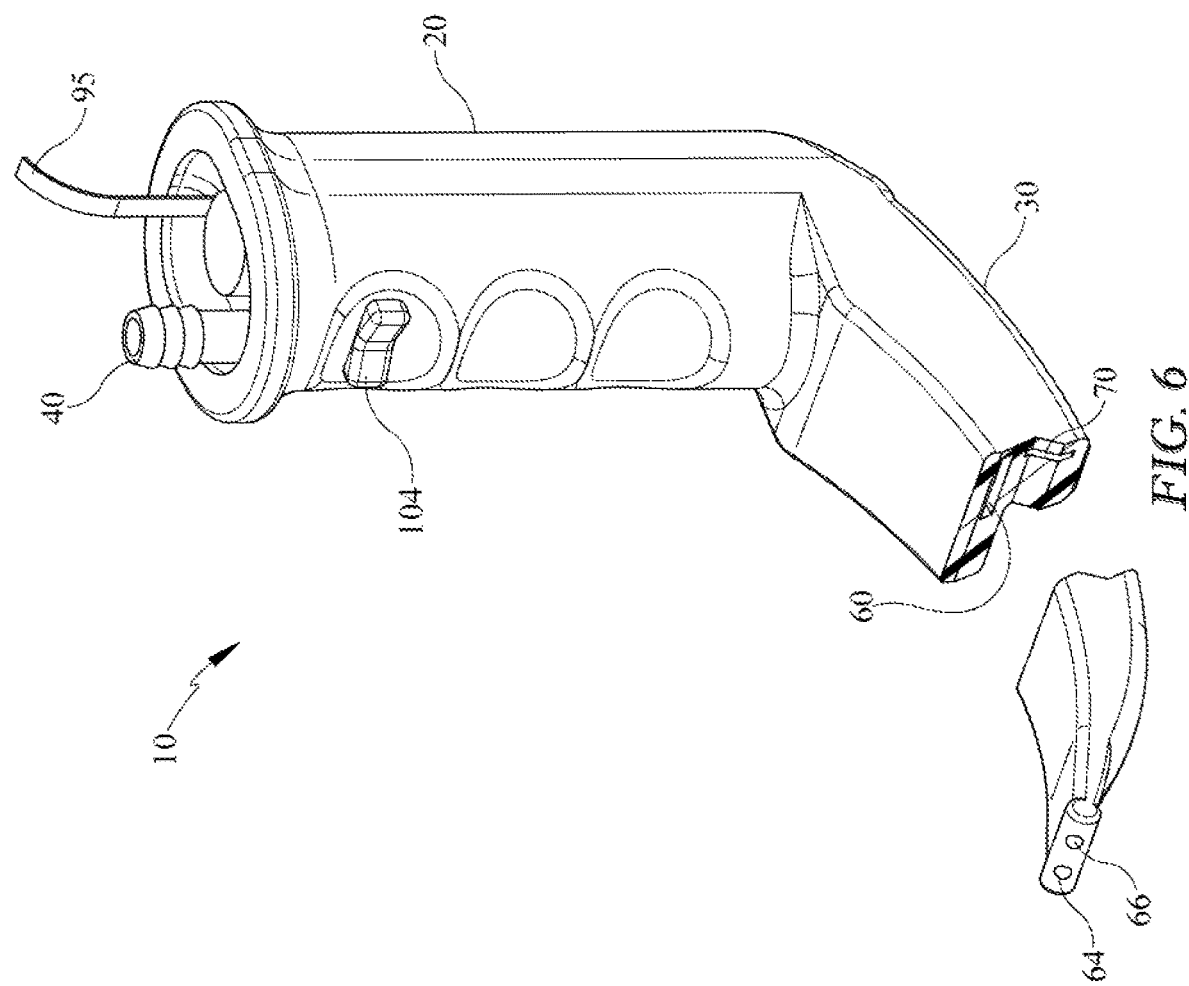
FIG. 6 is an alternate perspective view of the exemplary laryngoscope of FIG. 1, with a portion of the blade cutaway to illustrate the first and second internal channels that define the first and second air flow paths.

With respect to the camera lens 82, a camera 80 is housed within the blade, with the camera lens 82 oriented to look toward the distal end of the blade 30, as perhaps best shown in FIG. 3. In this exemplary embodiment, the blade is approximately six (6.0) inches in length, and the camera lens 82 is positioned approximately one and one-half (1.50) inches from the distal end of the blade 30. In any event, as mentioned above, the camera 80 is intended to provide a view of the glottis and vocal cords as the blade 30 of the laryngoscope 10 is inserted into the airway and used to lift the epiglottis. Because of the positioning of the two intake ports 74, 76, constant or intermittent suction can be applied to remove secretions in the vicinity of the camera lens 82 and maintain a clear view.

Figure 8:
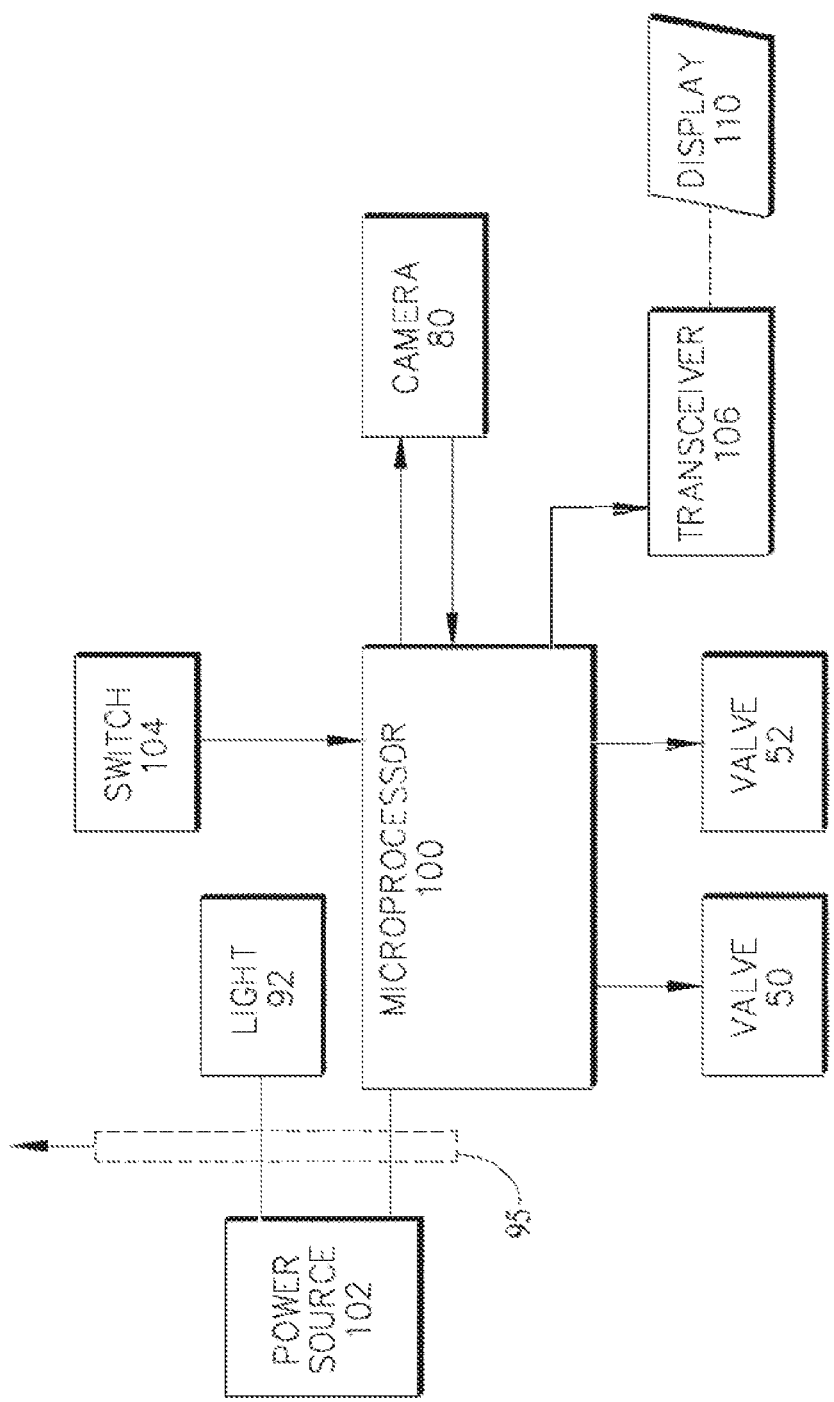
FIG. 8 is a schematic diagram of the control system of the exemplary laryngoscope of FIG. 1.

With respect to the control of the valves 50, 52, and the camera 80, an electronics package is preferably integrated into the handle 20 of the laryngoscope 10, as generally indicated by reference numeral 90 in FIGS. 2, 5-7, and 7A-7B. Referring now to FIG. 8, which is a schematic diagram of the control system in this exemplary embodiment, such an electronics package preferably includes a microprocessor (or microcontroller) 100 and a power source 102, such as one or more batteries. For example, one suitable microprocessor for use in the laryngoscope 10 of the present invention is a 16-bit Mixed Signal Microcontroller, Model No. MSP430I2020, manufactured and distributed by Texas Instruments Incorporated of Dallas, Tex.

Referring still to FIG. 8, each of the valves 50, 52 is operably connected to and in electrical communication with the microprocessor 100, which sends appropriate signals to the valves 50, 52 to cause each valve 50, 52 to open or close. In this regard, a switch 104 is also preferably connected to and is in electrical communication with the microprocessor 100. The switch 104 is used as an input means to instruct whether each valve 50, 52 should be opened or closed. In this regard, and as shown in FIGS. 2-7 and 7A-7B, in this exemplary embodiment, a three-position switch 104 is mounted on an exterior surface of the handle 20 of the laryngoscope 10. When the three-position switch 104 is in its static (or home) position, both valves 50, 52 are closed. When the switch 104 is depressed and toggled in one direction, the first valve 50 is open. When the switch 104 is depressed and toggled in an opposite direction, the second valve 52 is open.

Although a three-position switch 104 is described above, it should also be recognized that other switches and/or controls could also be used to open and close the valves 52, 52 and/or to provide constant or variable air flows through the first and second internal channels 60, 70 without departing from the spirit and scope of the present invention.

For example, in other embodiments, a laryngoscope made in accordance with the present invention may include independent buttons or switches on an exterior surface of the handle, such that the valves and resultant air flows could be independently controlled.

For another example, in other embodiments, a laryngoscope made in accordance with the present invention may include a mechanical switch, instead of an electrical switch. In other words, a switch would be mechanically linked to a valve or other obstruction in a respective flow path, and depression of the switch would thus cause the valve to open or the obstruction to be moved out of the flow path. For instance, a Manual Push Button Air Relief Valve, Model No. 14079, which is manufactured and distributed by Qosina Corp. of Edgewood, N.Y., could be integrated into the handle of a laryngoscope made in accordance with the present invention; such a valve includes an integral button or knob that facilitates opening of closing of the valve.

Referring still to FIG. 8, the camera 80 is also operably connected to and in electrical communication with the microprocessor 100, such that the microprocessor 100 can send an appropriate signal to the camera 80 to activate it. Once activated, digital signals from the camera 80 are then communicated back to the microprocessor 100. Once received by the microprocessor 100, such signals can then be transmitted to a remote display 110 (including, but not limited to a display on tablet computer or a smart phone), for example, using a wireless transceiver 106.

For example, one suitable camera for use in the laryngoscope 10 of the present invention is a Model No. OVM7692-RAAA image sensor manufactured and distributed by Digi-Key Corporation of Thief River Falls, Minn. One suitable wireless transceiver for use in the laryngoscope 10 of the present invention is an nBlue™ BR-LE4.0-S2A module manufactured and distributed by BlueRadios, Inc. of Englewood, Colo., which communicates using the Bluetooth® protocol. (Bluetooth® is a registered trademark of Bluetooth Sig, Inc. of Bellevue, Wash.)

Referring again to FIG. 1, in practice, the laryngoscope 10 may be maintained in sealed packaging (i.e., a sterile environment) until use. When needed, the laryngoscope 10 is removed from its packaging, a length of tubing 152 is used to connect the suction port 40 of the laryngoscope 10 to an air source 150, and the laryngoscope 10 is then introduced in the mouth of the patient.

While holding the laryngoscope 10 in one hand (e.g., the left hand), the physician or other medical professional can use his/her finger to manipulate the switch 104 to provide either intermittent or continuous suction via (i) the first air flow path and intake ports 64, 66, 68, which provide suction at the distal end (or tip) of the blade 30, or (ii) the second air flow path and intake ports 74, 76, which provide suction in the vicinity of the camera lens 82. For instance, in many cases, suction would be applied at the distal end (or tip) of the blade 30 via intake ports 64, 66, 68 during introduction of the laryngoscope 10.

As mentioned above, in other embodiments using independent switches or buttons, it would also be possible to provide intermittent or continuous suction via both the first and second air flow paths. For instance, if significant secretions were anticipated during introduction of the laryngoscope 10, intermittent or continuous suction could be provided both via (i) the first air flow path and intake ports 64, 66, 68 and (ii) the second air flow path and intake ports 74, 76.

When the physician or other medical professional is viewing the glottis, vocal cords, or other anatomical features as part of an indirect laryngoscopy, the camera 80 acquires the image, and then transmits it to a remote display 110 as described above. In such an indirect laryngoscopy, suction may also be provided via the second air flow path and intake ports 74, 76 at any time to remove secretions in the vicinity of the camera lens 82 and maintain a clear view.

Even in a direct laryngoscopy when the camera 80 is not used, providing suction via intake ports 74, 76 on the bottom surface of the blade 30 may still be useful in removing secretions and maintaining a good line of sight for the physician or other medical professional.

Furthermore, in the course of an intubation, the camera 80 of the laryngoscope 10 can also be used to capture static or video images of the glottis and vocal cords throughout the procedure.

As a further refinement, to assist the physician or other medical professional in the use of the laryngoscope 10, the laryngoscope 10 may also be provided with a light 92, such as a light-emitting diode (LED). As shown in FIG. 7, in this exemplary embodiment, the light 92 is positioned and directed to emit light down and along the blade 30 of the laryngoscope 10. In other words, in some embodiments, light would be directed along and would be emitted from a portion of the blade 30. Accordingly, in some embodiments, the blade 30 or at least a portion thereof would be made of a material that scatters light along the length of the blade 30, but ultimately allows light to exit through a lateral surface, for example, a frosted, translucent acrylic resin. In other embodiments, a section of the blade 30 (e.g., a section near the distal end) could be made from a transparent or translucent polycarbonate, so that light would be emitted from that transparent or translucent section. In other embodiments, the light 92 (or lights) may be positioned near the distal end of the blade 30 and/or near the camera lens 82.

Referring now to FIG. 8, to the extent that the laryngoscope 10 is provided with a light 92, the light 92 is powered by the power source 102 (such as one or more batteries). Furthermore, as an additional refinement, in this exemplary embodiment and as shown in FIGS. 2-7 and 7A-7B, a pull-tab 95 is provided and is used to physically block the contacts of the power source 102 and prevent it from providing power to the light 92 and/or microprocessor 100. Prior to use of the laryngoscope 10, the pull-tab 95 is removed, and the power source 102 is then electrically connected to the light 92 and/or microprocessor 100. For example, the pull-tab 95 may be positioned between the negative terminal of the battery and the corresponding circuit connection; such a pull-tab 95 would thus be made of a non-conductive material, such as polyethylene, nylon, polyvinyl chloride (PVC), or another thermoplastic.

Figure 9:
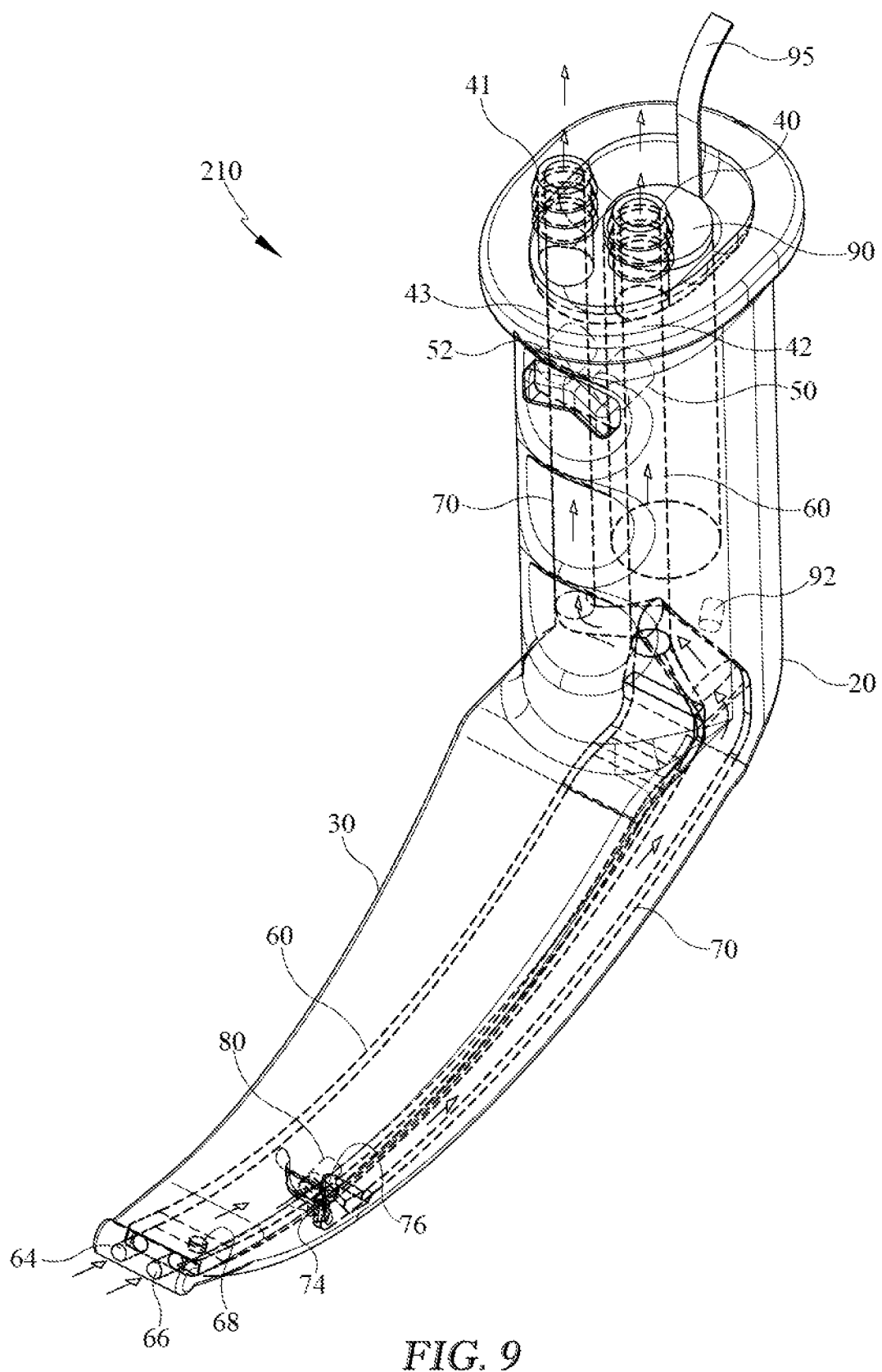
FIG. 9 is a perspective view of another exemplary laryngoscope made in accordance with the present invention.

FIG. 9 is a perspective view of another exemplary laryngoscope 210 made in accordance with the present invention. This exemplary laryngoscope 210 is identical to the one described above with respect to FIGS. 1-7, 7A-7B, and 8, with one difference. In this exemplary laryngoscope 210, there are two suction ports 40, 41 and two associated upper internal channels 42, 43 defined by the handle 20 of the laryngoscope 10. One upper internal channel 42 leads to the first valve 50, and the other upper internal channel 43 leads to the second valve 52. Thus, the first and second air flow paths are independent from the suction ports 40, 41 all the way through the laryngoscope 210 to intake ports 64, 66, 68 (for the first air flow path) and intake ports 74, 76 (for the second air flow path).

Irrespective of the particular embodiment, as a result of integrating suction functionality into the laryngoscope of the present invention, the physician or other medical professional can use the left hand to operate the laryngoscope and provide suction, while the right hand is used to manipulate an endotracheal tube 160 (FIG. 1) or for another purpose, such as externally manipulating the larynx to assist in image acquisition, retrieving foreign bodies from the airway, or performing a biopsy. Furthermore, the suction functionality is already in the mouth and immediately ready when needed, optimizing the speed at which suctioning of fluids that may be otherwise aspirated into the lungs. There is no need to locate, acquire, and position a suction catheter during the procedure, nor are there any delays caused by switching between manipulating the endotracheal tube and a separate suction catheter. There is also no risk of dropping and/or contaminating the endotracheal tube or the suction catheter during switches back and forth. There is also a reduced likelihood for procedure-related tissue damage, along with its associated bleeding and infection risk, because the laryngoscope is not being periodically removed and re-introduced into the mouth Furthermore, as result of the use of a specific suction pathway to remove secretions in the vicinity of the camera lens, a clear view of the glottis and vocal cords can be maintained at all relevant times. Without such a clear view, the physician or other medical professional may have to proceed without a clear view, which leads to increased risk for failed intubation or tissue damage, or the physician or other medical professional may have to start over with an alternative technique and/or new equipment, such as a more invasive airway procedure (e.g., a surgical airway), or cancellation of anesthesia plans for a needed surgery may occur.

Finally, it should be recognized that the laryngoscope of the present invention has potential uses beyond its use with an intubation. For example, the laryngoscope may be placed back into the mouth and throat after intubation to provide suction; indeed, the laryngoscope may be used as a dedicated suction device. For another example, the laryngoscope may be used to confirm placement of an endotracheal tube that has previously been placed. For yet another example, the laryngoscope may be used to clear the mouth and airway opening when no intubation is planned or when direct or indirect visualization of oral and throat tissues at or above the vocal cords is needed. For yet another example, the laryngoscope may be used to provide a clear view of the throat while freeing the right hand to operate a retrieval tool to remove foreign bodies from the airway, such as a small bone or chewing gum, at or above the vocal cords or to operate a biopsy or cautery tool. For yet another example, the laryngoscope may be used to apply direct pressure to bleeding tongue tissues, such as from a laceration or cancerous lesion, and assist in the localization of such lesions.

One of ordinary skill in the art will recognize that additional embodiments and implementations are also possible without departing from the teachings of the present invention. This detailed description, and particularly the specific details of the exemplary embodiments disclosed therein, is given primarily for clarity of understanding, and no unnecessary limitations are to be understood therefrom, for modifications will become obvious to those skilled in the art upon reading this disclosure and may be made without departing from the spirit or scope of the invention.

What is claimed is:

1. A laryngoscope, the laryngoscope comprising:
   a handle, said handle comprising an upper internal channel formed within the handle so that the handle and the upper internal channel comprise a single structure;
   a suction port configured for connection to an air source at a proximal end of the handle and formed within the handle so that the handle and the suction port comprise a single structure, said suction port defining an opening into the upper internal channel;
   a middle internal channel formed within the handle so that the handle and the middle internal channel comprise a single structure, said middle internal channel configured to (a) be operatively connected to at least one port to an external surface of the handle, said operative connection providing fluid communication between the middle internal channel and the at least one port, and (b) be transverse to the upper internal channel; and
   a blade formed in connection with the handle such that the handle and the blade comprise one structure, said blade comprising a first set of one or more intake ports and a second set of one or more intake ports;
   wherein the laryngoscope comprises a first lower internal channel with a non-circular profile formed within the blade that defines a first air flow path that extends from the upper internal channel to the first set of one or more intake ports,
   wherein the laryngoscope comprises a second lower internal channel with a non-circular profile formed within the blade that defines a second air flow path that extends from the upper internal channel to the second set of one or more intake ports,
   wherein the middle internal channel is configured to be interposed and provide fluid communication between (a) the upper internal channel and (b) the first and second lower internal channels such that the upper internal channel and the first and second lower internal channels are connected to the at least one port to the external surface of the handle by the middle internal channel, wherein the first lower internal channel, the second lower internal channel, the middle internal channel, the upper internal channel, the handle and the blade comprise a monolithic structure, and wherein the second set of one or more intake ports is located at a distance from the first set of one or more intake ports such that the second set of one or more intake ports applies suction in a different part of a patient anatomy from the first set of one or more intake ports.

2. The laryngoscope as recited in claim 1, the laryngoscope further comprising:

a first valve located at or close to the middle internal channel and interposed between the upper internal channel and the first lower internal channel to regulate air flow along the first air flow path; and a second valve located at or near the middle internal channel and interposed between the upper internal channel and the second lower internal channel to regulate air flow along the second air flow path.

3. The laryngoscope as recited in claim 2, wherein the first valve and the second valve inside the laryngoscope are operably connected to each other and at least one switch located at an exterior surface of the laryngoscope that overlay the first valve and the second valve, such that manipulation of the at least one switch is configured to cause the first valve to open or close in an opposing function to the second valve, thereby selectively opening or closing either the first or second lower internal channels.

4. The laryngoscope as recited in claim 2, wherein the first valve and the second valve are operably connected to at least one switch that is mounted on an exterior surface of the laryngoscope, such that manipulation of the at least one switch causes the first and second valves to open or close independently of each other, thereby allowing independent activation of the first and second lower internal channels.

5. The laryngoscope as recited in claim 1, wherein the first set of the one or more intake ports is positioned at a distal end of the blade.

6. The laryngoscope as recited in claim 1, and further comprising a camera housed within the blade for acquiring images during use of the laryngoscope, wherein the camera comprises at least one lens for acquiring the images, wherein the at least one lens is oriented perpendicular to an axis of the blade, and wherein the at least one lens is oriented perpendicular to an axis of the second lower internal channel.

7. The laryngoscope as recited in claim 6, and further comprising a wireless transceiver for transmitting the images acquired during use of the laryngoscope to a remote display, wherein the wireless transmitter is separated from the first and second lower internal channels by a wall, thereby preventing fluid contact with the wireless transceiver.

8. The laryngoscope as recited in claim 6, wherein the second set of one or more intake ports is positioned in the vicinity of the at least one lens of the camera, and wherein the second set of one or more intake ports has at least one intake positioned to direct suction flow across the at least one lens, thereby clearing the at least one lens of obstructions in vivo.

9. The laryngoscope as recited in claim 1, and further comprising a light that is positioned and directed to emit light along the blade of the laryngoscope.

* * * * *